United States Patent [19]

Terao et al.

[11] 4,011,214
[45] Mar. 8, 1977

[54] 3-(MORPHOLINOALKOXYIMINOME-THYL)CEPHEM COMPOUNDS

[75] Inventors: Shinji Terao; Mitsuru Shiraishi, both of Osaka; Toshio Miyawaki, Hyogo; Isao Minamida, Kyoto; Masayoshi Yamaoka; Mitsuo Numata, both of Osaka, all of Japan

[73] Assignee: Takeda Chemical Industries, Ltd., Japan

[22] Filed: Dec. 20, 1974

[21] Appl. No.: 534,787

[30] Foreign Application Priority Data

Dec. 20, 1973 Japan .......................... 48-143175

[52] U.S. Cl. .................... 260/240 G; 260/243 C; 424/246
[51] Int. Cl.² ............ C07D 501/50; C07D 501/52; C07D 501/54
[58] Field of Search .................. 260/243 C, 240 G

[56] References Cited

UNITED STATES PATENTS 3,855,213  12/1974  Dunn et al. ................... 260/243 C
3,867,380  2/1975  Dunn et al. ................... 260/243 C

FOREIGN PATENTS OR APPLICATIONS 7,309,511  1/1974  Netherlands

Primary Examiner—Nicholas S. Rizzo
Assistant Examiner—Diana G. Rivers
Attorney, Agent, or Firm—Craig & Antonelli

[57] ABSTRACT

Novel cephalosporin compounds of the formula

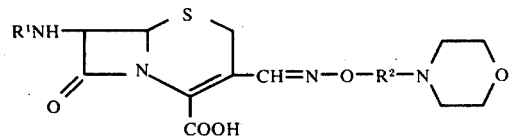

wherein $R^1$ is an acyl group and $R^2$ is an alkylene group which may be substituted with a lower alkoxyl group, or pharmaceutically acceptable salt thereof, have strong inhibitory actions on broad spectra of gram-positive and gram-negative bacteria and, particularly against *Esherichia coli* and *Klebsiella pneumoniae*. Thus, the compounds are useful as therapeutic agent for various bacterial infections of animals including human beings.

23 Claims, No Drawings

3-(MORPHOLINOALKOXYIMINOMETHYL)-CEPHEM COMPOUNDS

The present invention relates to novel and useful cephaloaporin compounds and to a method for preparing them, and more particularly to compounds of the formula:

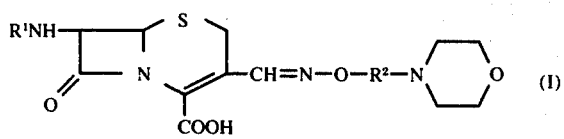

wherein $R^1$ is an acyl group and $R^2$ is an alkylene group which may be substituted with a lower alkoxyl group.

Previously, the present inventors established an abridged method by which a cephalosporin-lactol derivative of the formula:

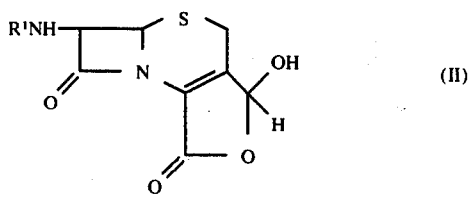

(wherein $R^1$ is as hereinbefore defined) can be easily produced from 3-hydroxymethyl-cephalosporin derivative of the formula:

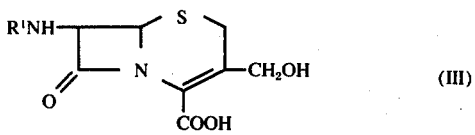

(wherein $R^1$ is as hereinbefore defined). This method has already been published by Belgian Pat. No. 808341 and Offenlegungsschrift 2360620 of West Germany. Based on this research work, the inventors tried to have a cephalosporin-lactol derivative (II) react with an O-(morpholinoalkyl)hydroxylamine of the formula:

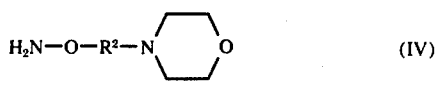

(wherein $R^2$ is as hereinbefore defined) and acylate an aminocephalosporanic acid derivative of the formula:

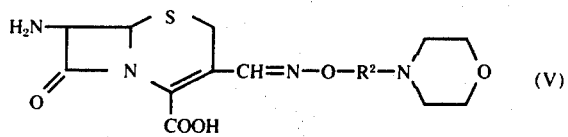

(wherein $R^2$ is as hereinbefore defined) to produce 3-(morpholinoalkoxyiminomethyl)cephem compound (I) and then discovered that the compound (I) is stable compound which has strong inhibitory actions on broad spectra of gram-positive and gram-negative bacteria and, particularly against Escherichia coli and Klebsiella pneumoniae, more potent activities than any known cephalosporin.

This invention has been developed on the basis of the above findings.

It is the principal object of the present invention to provide the novel and useful compound (I).

Another object of the present invention is to provide a method for producing compound (I).

A further object is to provide new pharmaceutical compositions containing compound (I).

Other objects of the present invention and advantageous features thereof will become apparent as the description proceeds.

Referring to starting material (II) which is employed in the first-mentioned process of this invention, the acyl group designated by symbol $R^1$ is preferably one of the acyl groups found in the corresponding moieties of penicillins and cephalosporin derivatives, particularly a substituted oxyacetyl group such as phenoxyacetyl, phenoxypropionyl or the like, but may also be any of the following: Aliphatic carboxylic acid acyl groups such as formyl, acetyl, propionoyl, hexanoyl, outanoyl, heptanoyl, octanoyl, cyclopentanoyl, etc.; mono-substituted aliphatic carboxylic acid acyl groups such as phenylacetyl, cyclohexylacetyl, 1-cyclohexenylacetyl, 1,4-cyclohexadienylacetyl, 2-thienylacetyl, tetrazolylthioacetyl, tetrazolylacetyl, cyanoacetyl, phenoxyacetyl, acetoacetyl, 4-methylthio-3-oxobutyryl, 4-carbamoylmethylthio-3-oxobutyryl, α-phenoxypropionyl, α-phenoxybutyroyl, α-(p-nitrophenoxy)-acetyl, α-(p-aminophenoxy)propionyl, p-nitrophenylacetyl, phenylpropionyl, butylthioacetyl, α-(p-chlorophenoxy)acetyl, α-(2-pyridyloxy)acetyl, α-(3-pyridyloxy)acetyl, α-(4-pyridyloxy)-acetyl, phenylthioacetyl, chlorophenylthioacetyl, benzylthioacetyl, phenethylthioacetyl, allylthioacetyl, 4-pyridylthioacetyl, benzylthiopropionyl, (1-imino-2-phenylethyl)aminoacetyl, 2-(3-sydnone)acetyl, 1-pyrazolylacetyl, 4-nitro-1-pyrazolylacetyl, 4-chloro-1-pyrazolylacetyl, 3,5-dimethyl-1-pyrazolylacetyl, 2-furylacetyl, 6-(2'-oxo-3'-methylpyradizinyl)-thioacetyl, etc.; di-substituted aliphatic carboxylic acid acyl groups such as α-carboxylphenylacetyl, α-bromopropionyl, α-aminophenylacetyl, mandelyl, α-sulfophenylacetyl, α-sulfo-(p-aminophenyl)acetyl, 1-cyclohexenylglycyl, thienylglycyl, furylglycyl, cyclohexadienylglycyl, phenylmethylglycyl, carbamoylphenylacetyl, 5-amino-5-carboxyvaleryl, 5-carboxy5-(2'-dialkyl-3',5'-dicarboalkoxy1',4'-dihydropyrido-1'-yl)valeryl, 5-phenylacetylamino-5-carboxyvaleryl, 5-benzoylamino-5-carboxyvaleryl, 5-(p-toluenesulfonyl)amino-5-carboxyvaleryl, 5-(benzyloxycarbonyl)-amino-5-carboxyvaleryl, α-(β-methylsulfonylethoxycarbonyl)-aminophenylacetyl, etc.; acryloyl; aromatic acyl groups such as berzoyl, 2,6-dimethoxybenzoyl, 2-ethoxynaphthoyl, 2-phenylbenzoyl, p-nitrobenzoyl, etc.; heterocyclic acyl groups such as 5-methyl-3-phenyl-4-isoxazolylcarbonyl, 3-o-chlorophenyl-5-methyl-4-isooxazolylcarbonyl, 3-(2,6-dichlorophenyl)-5-methyl-4-isooxazolycarbonyl, etc.; for instance. When such acyl groups have amino groups, they may be protected by such groups as alkyloxycarbonyl (e.g. isobornyloxycarbonyl, etc.), β-alkylsulfonylethoxycarbonyl (e.g. β-methylsulfonylethoxycarbonyl, etc.), arylcarbonyl which may be substituted with tert-lower alkyl group (e.g. benzoyl, phthalyl, p-t-butylbenzoyl, etc.), aralkylcarbonyl (e.g. phenylacetyl, etc.), arylthiocarbonyl (e.g. phenylthiocarbonyl, etc.), aralkyloxycarbonyl (e.g. benzyloxycarbonyl, etc.), arylsulfonyl which may be substituted with lower alkyl group (e.g. p-toluenesulfonyl, p-t-butylbenzenesulfonyl, etc.) or so.

More desirably, acyl groups are formyl, benzoyl or the group tetrazolyl, a formula:

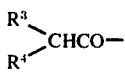

wherein $R^3$ is hydrogen, phenyl, phenoxy, thienyl, tetrzolyl, furyl, pyrazolyl, pyridyloxy, cyclohexenyl, acetyl, cyano, 3-amino-3-carboxypropyl, 3-protected amino-3-carboxypropyl, and $R^4$ is hydrogen, hydroxyl, sulfo, amino, carboxyl or lower alkyl group.

Each of these cephalosporinlactol derivatives (II) exists in equilibrium with an aldehyde compound (VI), which is a tautomer of the former, as indicated below in formulas.

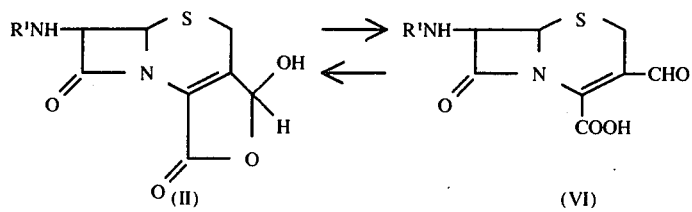

This equilibrium is affected to a significant extent by the pH of the solution, the polarity of the solvent and other factors.

The hydroxyl group of the cephalosporinlactol derivative (II) may have been replaced by an alkoxyl group, e.g. methoxy, ethoxy or propoxy, or an acyloxy group, e.g. acetoxy.

Also useful are various esters at 4-carboxyl function of the aldehyde compound (VI) (Japanese Patent Application Laid Open 68594/1973). As said esters, use may commonly be made of easily clearable esters of pharmaceutically acceptable esters hereinafter described.

Both the cases are subsumed in the meaning of the cephalosporinlactol derivatives (II) useful for the reaction of this invention.

Referring to the other starting compound (IV), the alkylene group designated by symbol $R^2$ may be any of such alkylene groups as methylene, ethylene, trimethylene, tetramethylene; 1-methylethylene, 2-methylethylene, 1-methylpropylene, 2-methylpropylene, 3-methylpropylene, 1,1-dimethylethylene, etc. These alkylene groups may have such substituents as alkoxyls, e.g. methoxy, ethoxy, etc. Each of these o-(morpholinoalkyl)hydroxylamine is subjected to the contemplated reaction, either in the free form or in other forms such as salts with acids, e.g. hydrochloric acid, sulfuric acid, acetic acid, etc.

The reaction of the cephalosporinlactol derivative (II) with o-(morpholinoalkyl)hydroxylamine (IV) is usually achieved by mixing them in equimolar proportions in a solvent, although their ratio may be varied within reasonable limits. While the solvent may be any solvent that will not adversely affect the reaction, it is advantageous to employ, above all else, dimethylsulfoxide, dimethylformamide, tetrahydrofuran, dioxane, ethyl acetate, acetonitrile, and sulfolane, as well as suitable mixtures of such solvents, etc. In most instances, the reaction goes to completion within 1 to 8 hours. The o-(morpholinoalkyl)hydroxylamine may be used as the corresponding salt of a strong acid. e.g. hydrochloride or sulfate. In such a case, the reaction will at times proceed more smoothly if an alkali metal salt of a weak acid, such as sodium acetate, potassium acetate or sodium hydrogen carbonate is added to the reaction system.

The procedures that may be followed for the isolation and purification of thus-obtained 3-(morpholinoalkoxyiminomethyl)cephem compound (I) vary, in fine detail, with the particular combination of $R^1$ and $R^2$ but usually the compound (I) can be separated and purified by known procedures such as solvent extraction, chromatography using an ion exchange resin, polystyrene resin, silica gel, cephadex resin, etc. as adsorbents or molecular sieves, or/and recrystallization.

The 3-(morpholinoalkoxyiminomethyl)cephem compound (I) thus obtained may be put to use with its 4-carboxyl group being free or, alternatively, in the form of a salt with a nontoxic cation, e.g. sodium, potassium or the like; a basic amino acid, e.g. arginine, ornithine, lysine, histidine or the like; or a polyhydroxyalkylamine, e.g. N-methylglucamine, diethanolamine, triethanolamine, tris-hydroxymethylaminomethane or the like.

The cephalosporinlactol derivative (II) that is employed in the above reaction can be easily produced by oxidizing a 3-hydroxymethylcephalosporin derivative of the formula:

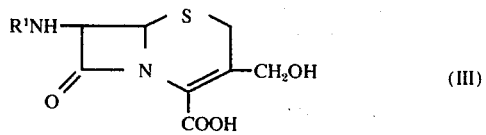

(wherein $R^1$ is as hereinbefore defined) or an alkali metal salt or ester thereof with a hexavalent chromium compound.

The 3-(morpholinoalkoxyiminomethyl)cephem compounds (I) of this invention can also be produced by acylating an aminocephalosporanic acid derivative (V). The aminocephalosporanic acid derivative (V) to be thus used in the acylation reaction can be produced by the scission, in a manner that is conventional per se, of the 7-acyl group from the corresponding acyl derivative such as, 7β-[D-5-(p-t-butylbenzoyl)amino-5-carboxyvaleramido]-3-morpholinoalkyloxyiminomethyl-3-cephem-4-carboxylic acid or 7β-[D-5-(p-t-butylbenzenesulfonyl)amino-5-carboxyvaleramido]-3-morpholinoalkyloxyiminomethyl-3-cephem-4-carboxylic acid and is subjected to the contemplated reaction in its free form or as a salt or easily cleavable ester. As the salt just mentioned, there may be employed the corresponding salts of alkali or alkaline earth metals or of organic amines, such as the salts of sodium, potassium, magnesium, aluminum, trimethylamine, triethylamine, tributylamine, etc. As the easily cleavable ester, there may be employed the products of reaction of the aminocephalosporanic acid derivative (V) with silylating agents such as trialkylhalogenosilanes, triaralkylhalogenosilanes, trialkoxyhalogenosilanes, hexaalkyldisilazane, N,O-bis(trimethylsilyl)acetamido, etc.; silenating agents such as dialkyldihalogenosilanes, diaralkyldihalogenosilanes, etc.; tinesterifying agents such as tin oxide(trialkyl tin), N-trialkylstannyldialkylamines, trialkylstannyl alkoxides, etc.; and the reaction products of the aminocephalosporanic acid derivative (V) with alkylsulfonylalkyl halides, alkylthioalkyl halides, etc.

The acylation reaction is carried out by permitting a carboxylic acid, which is to be introduced into the aminocephalosporanic acid derivative (V), or a reactive derivative thereof to act upon the aminocephalosporanic acid derivative (V). As said reactive derivative, there may be mentioned, among others, the corresponding acid halides, e.g. acid chloride, acid bromide, etc.; the acid anhydrides with alkyl carbonates, alkyl phosphates, other carboxylic acids, etc.; activated esters of the carboxylic acid with pentachlorophenol, p-nitrophenol, N-hydroxysuccinimide, etc.; and the reactive derivatives of the carboxylic acid with condensing agents such as carbodiimides, N,N'-carbonyldiimidazole, acetylene, ethers, etc. Among the more common species of said carboxylic acid to be introduced are those having the acyl groups mentioned hereinbefore for $R^1$.

The acylation reaction is ordinarily conducted in a solvent. Among the solvents suited for this purpose are such common organic solvents as acetone, dioxane, chloroform, methylene chloride, tetrahydrofurn, ether, ethyl acetate, etc., and depending upon the particular starting compound employed, the reaction may be carried out in water or an aqueous solvent. While there is no particular limitation upon the reaction temperature, the reaction is in many cases conducted under cooling or at room temperature. In connection with this reaction, the contemplated compound (I) may be produced as the inner salt or as a salt by permitting a base to be present in the reaction system. The base just mentioned may, for example, be an alkali hydrogen carbonate, alkali carbonate, alkali hydroxide or an organic amine, e.g. triethylamine, pyridine or N,N-dimethylaniline. When the starting material is an ester of aminocephalosporanic acid derivative (V), hydrolysis, if required is carried out in a per se known manner and the reaction product may be recovered by a conventional procedure such as solvent extraction. chromatography or the like and, if necessary, purified by recrystallization or other procedure.

The 3-(morpholinoalkoxyiminomethyl)cephem compounds (I) obtained by the foregoing method of this invention may be used with its carboxyl group in 4-position being free but may also be put to use with said carboxyl function having been previously converted to a salt, for example, by use of a nontoxic cation, e.g. sodium, potassium or the like; a basic amino acid, e.g. arginine, ornithine, lysine, histidine or the like; or a polyhydroxylalkylamine, e.g. N-methylglucamine, diethanolamine, triethanolamine, tris-hydroxymethylamine-methane or the like. It is also possible to esterify the 4-carboxyl function of the compound to produce biologically active ester derivatives that provide elevated blood levels and prolonged action.

The ester residues useful for this purpose are $\alpha$alkoxy-$\alpha$-substituted methyl groups such as alkoxymethyl, $\alpha$-alkoxyethyl or the like, for example, methoxymethyl, ethoxymethyl, isopropoxymethyl, $\alpha$-methoxyethyl, $\alpha$-ethoxyethyl, etc.; alkylthiomethyl groups such as methylthiomethyl, ethylthiomethyl, isopropylthiomethyl, etc.; and acyloxymethyl groups or $\alpha$-acyloxy-$\alpha$-substituted methyl groups such as pivoloyloxymethyl, $\alpha$-acetoxybutyl, etc., to name but a few.

The 3-(morpholinoalkoxyiminomethyl)cephem compounds (I) thus obtained are cephalosporin derivatives which are not only new but also have potent antimicrobial activity against gram-negative and gram-positive bacteria, thus being of precious value as drugs for the therapy of infectious diseases in animals including human beings. Like known cephalosporin products, the contemplated compounds (I) of this invention can be administered for example in the form of powders or as solutions or suspensions which can be obtained in the routine manner with a physiologically acceptable vehicle or excipient. For instance, in the treatment of infectious diseases in man, the contemplated compounds (I) of this invention, e.g. 7$\beta$-(2-thienylacetamido)-3-(2-morpholinoethoxy)iminomethyl-3-cephem-4-carboxylic acid. 7$\beta$-(D-mandelylamido)-3-(2-morpholinoethoxy)-iminomethyl-3-cephem-4-carboxylic acid and 7$\beta$-($\alpha$-sulfophenylacetamido)-3-(2-morpholinoethoxy)iminomethyl-3-cephem-4-carboxylic acid sodium salt, are each desirably administered parenterally (non-orally) at the daily dose level of about 5 to 20 milligrams per kilogram body weight in 3 to 4 divided doses per day.

The NMR spectra in the examples to be given hereinafter were obtained using a spectrometer Varian T-60 or HR-100. The chemical shifts were expressed in parts per million (p.p.m.) relative to internal tetramethylsilane ($\delta$). Unless otherwise specified, deuteriochloroform was used as the solvent. The symbol $s$ signifies a singlet, $d$ a doublet, $t$ a triplet, $q$ a quartet, ABq a AB type quartet, $m$ a multiplet and J a coupling constant in Herz.

It is to be understood that the following examples are solely for the purpose of illustration and not to be construed as limitations of this invention, and that many variations may be resorted to without departing from the spirit and scope of this invention. In this specification, g., 1. and ml., are gram, liter and milliliter respectively. Further, DMSO means dimethylsulfoxide, nm nano meter, IR significant absorption bands in infrared spectrum and UV absorption in ultraviolet absorption spectrum, respectively. Resins named "Amberlite" are manufactured products by Rohm & Haas Co. in U.S.A. Temperatures are all uncorrected, and percentages are all on weight basis.

EXAMPLE 1

(1) N-[p-(t-butyl)-benzoyl]-cephalosporin C

To cephalosporin C monosodium (47.4 g.) are added water (500 ml.) and acetone (150 ml.) and the mixture is maintained at 3° – 4° C.

Under stirring, the mixture is adjusted to pH 9 with sodium carbonate powder and, then, p-(t-butyl)-benzoyl chloride (21.5 g.) is added dropwise over a period of 1.5 hours. During the dropwise addition, the pH is maintained at 9.0 with sodium carbonate powder. The mixture is further stirred at 15° C and pH 9.0 for 1.5 hours, after which it is adjusted to pH 7.0 with phosphoric acid and most of the acetone is distilled off under reduced pressure. The concentrate is washed twice with ethyl acetate (400 ml.) and fed to a separatory funnel. The equeous layer is cooled to 5° C and, under stirring, the pH is brought to 2.5 with phosphoric acid. The solution is extracted three times with ethyl acetate (600 ml.). The extracts are pooled, dried over anhydrous sodium sulfate and concentrated to dryness under reduced pressure. The described procedure gives N-[p (t-butyl)-benzoyl]-cephalosporin C.

IR: 1778, 1730, 1708, 1680, 1660, 1540cm$^{-1}$. NMR($d_6$-DMSO)$\delta$: 1.28(9H), approx. 1.5 – 1.9(4H), 2.01(3H), 2.10 – 2.35(2H), 3.36 and 3.61(2H, ABq), 4.37(1H), 4.68 and 4.99(2H, ABq), 5.06(1H), 5.67(1H), 7.46 and 7.82(4H, ABq), 8.41(1H), 8.79(1H)

(2) Disodium
7$\beta$-[D-5-(p-t-butylbenzamido)-5-carboxyvaleramido]-3-hydroxymethyl-3-cephem-4-carboxylate In phosphate buffer of pH 7.2(1 l.) is dissolved N-[p-(t-butyl)-benzoyl]-cephalosporin C disodium (47 g.), followed by the addition of lipase "Saiken 100" (manufactured by Osaka Saikin Kenkusho) (50 g.).

The system is reacted on a water bath at 30° C with stirring for 18 hours. During this period, an aqueous solution of sodium hydrogen carbonate is added from time to time so that the pH of the system will not drop below 7.2. After the reaction, the solution is cooled (to 5° C) and its pH is adjusted to 2.90 with phosphoric acid. To this is added ethyl acetate (1 l.), followed by thorough stirring. Since this mixture contains the insoluble enzyme, it is filtered over celite. The celite as well as insolubles are washed well with ethyl acetate (500 ml.). The filtrate and the ethyl acetate washing are combined and fed to a separatory funnel. The organic layer is washed with water (100 ml. × 3) and shaken well with a 3 % aqueous solution of sodium hydrogen carbonate. The aqueous sodium hydrogen carbonate solution is added gradually until the pH of the aqueous layer is 5.50. The aqueous layer seperated is adjusted to pH 7.0 with 2N aqueous sodium hydroxide and, then, freeze-dried. The above procedure gives disodium 7$\beta$-[D-5-p-(t-butyl)-benzamido-5-carboxylvaleramido]-3-hydroxymethyl-3-cephem-4-carboxylate.

IR: 1760 cm$^{-1}$. NMR($D_2O$)$\delta$: 1.25(9H), 3.27 and 3.57(2H, ABq), 4.30(2H), 5.07(1H), 5.68(1H), 7.50 and 7.84(4H, ABq)

(3)
7$\beta$-[D-5-(p-t-butylbenzoyl)amino-5-carboxyvaleramido]-9-oxo-11-hydroxy-11H-furano(4,3-c)-3-cephem.

To the 3-hydroxymethyl-cephalosporin derivative obtained in (2) above (2.5 g.) is added acetone (80 ml.) and the resultant suspension is stirred under cooling at 5° C. To this is added a chromic acid-sulfuric acid mixture (1.88 ml.) [prepared by adding concentrated sulfuric acid (4.52 ml., $H_2SO_4$ content 1.77 g./ml.) to chromic anhydride (2.67 g., choice reagent grade) and diluting the mixture carefully with water to make a total of 15.0 ml.]dropwise over a period of 3 minutes, followed by stirring at 5° C for a further 20 minutes. After the reaction has been completed, most of the acetone is distilled off and the residue is diluted with water (30 ml.) and extracted three times with ethyl acetate (50 ml.). The ethyl acetate solution is dried over anhydrous sodium sulfate and concentrated to dryness under reduced pressure.

The procedure gives 7$\beta$-[D-5-(p-t-butylbenzoyl)amino-5-carboxyvaleramido]-9-oxo-11-hydroxy-11H-furano(4,3-c)-3-cephem.

(4) Monosodium 7$\beta$-[D-5-(p-t-butylbenzoyl)amino-5-carboxyvaleramido]-3-(2-morpholinoethoxy)iminomethyl-3-cepham-4-carboxylate.

In dimethylsulfoxide (20 ml.) is dissolved 7$\beta$-[D-5-(p-t-butylbenzoyl)amino-5-carboxyvaleramido]-9-oxo-11-hydroxy-11H-furan(4,3-c)-3-cephem(2.8 g.). Then, 0-(2-morpholinoethyl)hydroxylamine dihydrochloride (1.0 g.) is added in a single dose and the mixture is stirred at room temperature for 1 hour. To this solution, anhydrous sodium acetate (0.431 g.) is added over a period of 1 hour, after which the mixture is further stirred for 2 hours. The reaction mixture is diluted with cold water (10 ml.) and adjusted to pH 7 with 10 % aqueous sodium hydrogen carbonate. It is then subjected to column chromatography on polystyrene resin (Amberlite XAD-2) and developed with water and, then, with 20 % aqueous ethanol. The fractions obtained by elution with 20% aqueous ethanol are pooled and freeze-dried to recover the captioned compound. Yield 1.2 g. (33.8 %)

IR(KBr): 1775, 1605 cm$^{-1}$. NMR($D_2O$)$\delta$: 1.31(s,t-Bu), 1.5 – 2.2(m, —(CH$_2$)$_2$—), 2.3 – 2.6(m, —CH$_2$CO); 2.6 – 2.9(m, morpholine $\beta$—CH$_2$ and —CH$_2$—N=), 3.44 and 3.72(ABq, J=18Hz, 2—CH$_2$), 3.82(m, morpholine $\alpha$—CH$_2$), 4.30(m, OCH$_2$—), 4.54(m, valeryl—CH=), 5.17(d, J=5Hz, 6—H), 5.74(d, J=5Hz, 7—H), 7.56 and 7.88(each e, J=8Hz, benzene), 8.26(s, —CH=NO—)

EXAMPLE 2

(1) N-[p-(t-butyl)-benzenesulfonyl]-cephalosporin C

In a procedure similar to (1) in Example 1, p-(t-butyl)-benzenesulfonyl chloride is used instead of p-(t-butyl)-benzoyl chloride, whereby the captioned compound is obtained. Yield 51.9 g.

IR(KBr): 1770, 1728, 1710, 1660 cm$^{-1}$ NMR($d_6$-DMSO)$\delta$: 1.29(9H), 2.01(3H), 3.40 and 3.64(2H, ABq), 4.70 and 5.02(2H, ABq), 5.06(1H, d), 5.64(1H, q), 7.50 and 7.68(4H, ABq), 7.94(1H, d), 8.72(1H, d)

(2) Disodium 7$\beta$-[D-5-(p-t-butylbenzenesulfonyl)amino-5-carboxyvaleramido]-3-hydroxymethyl-3-cephem-4-carboxylate In phosphate buffer of pH 7.2 (1 l.) is dissolved N-[p-(t-butyl)-benzenesulfonyl]-cephalosporin C disodium (50 g.), followed by the addition of lipase "Saiken 100" (manufactured by Osaka Saikin Kenkusho) (50 g.). The system is reacted on a water bath at 30° C with stirring for 18 hours. During this period, an aqueous solution of sodium hydrogen carbonate is added from time to time for keeping the pH of the system higher than 7.2. After completion of the reaction, the reaction mixture is cooled (to 5° C) and adjusted its pH to 2.90 with phosphoric acid. To the resultant mixture is added ethyl acetate (1 l.) and stirred thoroughly, followed by filtration of the insoluble enzyme using celite as filter aid. The filter cake is washed well with ethyl acetate (500 ml.). The filtrate and the ethyl acetate washing are combined and the mixture is well shaken. The organic layer is washed with water (100 ml. × 3) and shaken well with a 3 % aqeuous solution of sodium hydrogen carbonate. To the aqueous layer is added gradually an aqueous solution of sodium hydrogen carbonate until its pH becomes 5.50, and pH of the resultant solution is adjusted to 7.0 with a 2N aqueous solution of sodium hydroxide and then, freeze-dried. The above procedure gives the captioned compound.

IR: 1754, 1660, 1595 cm$^{-1}$. NMR(D$_2$O)$\delta$: 1.30(9H), 4.36(2H), 5.15(1H, d), 5.68(1H, d), 7.60 and 7.86(4H, ABq)

(3) 7$\beta$-[D-5-(p-t-butylbenzenesulfonyl)amino-5-carboxyvaleramido]-9-oxo-11-hydroxy-11H-furano(4,3-c)-3-cephem A suspension of disodium 7$\beta$-[D-5-(p-t-butylbenzenesulfonyl)amino-5-carboxyvaleramido]-3-hydroxymethyl-3-cephem-4-carboxylate in 300 ml. of acetone is stirred under cooling at 5° C. And to the suspension is added a chromic acid - sulfuric acid mixture (6.10 ml.) [prepared in a procedure similar to (1) in Example 1] dropwise over a period of 5 minutes, followed by stirring at 5° C for further 15 minutes. After the reaction has been completed, most of the acetone is distilled off under reduced pressure and the residue is diluted with water (250 ml.) and then the mixture thus obtained is extracted two times with ethyl acetate (300 ml.). The combined ethyl acetate extracts are washed twice with a saturated aqueous solution (300 ml.) of sodium chloride, dried over anhydrous sodium sulfate, and concentrated to dryness. The procedure gives the above-indicated compound. Yield 7.3 g (78.9 %)

(4) Monosodium 7$\beta$-[D-5-(p-t-butylbenzenesulfonyl)amino-5-carboxyvaleramido]-3-(2-morpholinoethoxy)iminomethyl-3-cephem-4-carboxylate In dry dimethylsulfoxide (70 ml.) is dissolved 7$\beta$-[D-5-(p-t-butylbenzenesulfonyl)amino-5-carboxyvaleramido]-9-oxo-11-hydroxy-11H-furano(4,3-c)-3-cephem (5.67 g.), followed by the addition, in a single dose, of 0-(2-morpholinoethyl) hydroxylamine dihydrochloride (2.19 g.). The mixture is stirred at room temperature for 3 hours, after which sodium hydrogen carbonate (3.36 g.) in water (40 ml.) are added. The solution is developed on a column of polystyrene resin (Amberlite XAD-2) with water and, then, with 15 % aqueous ethanol. The fractions containing the contemplated product are pooled and, after the ethanol is distilled off under reduced pressure, freeze-dried. The procedure gives the captioned compound.

Yield 2.29 g. (32 %). IR(KBr): 1764, 1655, 1599cm$^{-1}$. NMR(D$_2$O)$\delta$: 1.37(s,t—Bu), 1.63(m, —CH$_2$CH$_2$—), 2.19(m, —CH$_2$CONH—) 2.7 – 3.0(m, morpholine $\beta$—CH$_2$ and —CH$_2$N=), 3.5 – 4.0(m, 2—CH$_2$, morpholine $\alpha$—CH$_2$ and valeryl —CH=), 4.32(m, =NO—CH$_2$—), 5.21(d, J=5Hz, 6—H), 5.77(d, J=5Hz, 7—H), 7.62 and 7.90 (each d, J=9Hz, benzene), 8.32 (s, —CH=N—)

EXAMPLE 3

7$\beta$-(phenylacetamido)-3-(2-morpholinoethoxy)iminomethyl-3-cephem-4-carboxylic acid In dry dimethylsulfoxide (10 ml.) is dissolved 7$\beta$-(phenylacetamido)-9-oxo-11-hydroxy-11H-furano-(4,3-c)-3-cephem (0.346 g.), followed by the addition, in a single dose, of 0-(2-morpholinoethyl)hydroxylamine dihydrochloride (0.219 g.). The mixture is stirred at room temperature for 30 minutes. To this mixture is added anhydrous sodium acetate (0.082 g.) over a period of 2 hours, after which the mixture is further stirred at room temperature for 1 hour.

To this is added a solution of sodium acetate (0.164 g.) in water (10 ml.) under cooling and the resultant mixture is developed on a column of polystyrene resin (Amberlite XAD-2), first with water, then with 5% aqueous ethanol and finally with 15% aqueous ethanol. The fractions containing the desired product are pooled and the ethanol is distilled off. The residue is freeze-dried, whereupon the captioned compound is obtained.

Yield 0.412 g. (87 %). IR(KBr): 1765, 1665, 1605 cm$^{-1}$ NMR(D$_2$O)$\delta$: 2.6 – 3.0(m, morpholine $\beta$—CH$_2$), 3.5 – 3.8(m, 2—CH$_2$ and morpholine $\alpha$—CH$_2$ and —CH$_2$CO), 4.20(m, —CH$_2{}^+$NH=), 4.70(m, =NOCH$_2$—), 5.07(d, J=5Hz, 6—H), 5.60(d, J=5Hz, 7—H), 7.25(s, benzene), 8.38(s, —CH=N—)

EXAMPLE 4

7$\beta$-(2-thienylacetamido)-3-(2-morpholinoethoxy)iminomethyl-3-cephem-4-carboxylic acid In dry dimethylsulfoxide (10 ml.) is dissolved 7$\beta$-(2-thienylacetamido)-9-oxo-11-hydroxy-11H-furano(4,3-c)-3-cephem (0.352 g.) and, then, 0-(2-morpholinoethyl) hydroxylamine dihydrochloride (0.219 g.) is added in a single dose. The mixture is stirred at room temperature for 1 hour. To this mixture is added anhydrous sodium acetate (0.082 g.) over a period of 1 hour, after which the mixture is further stirred at room temperature for 1 hour. Then, a solution of sodium acetate (0.33 g.) in water (10 ml.) is added and the resultant mixture is developed on a column of polystyrene resin (Amberlite XAD-2) with water and, then, with 20 % aqueous ethanol. The fractions containing the contemplated product are pooled and, after the ethanol is distilled off, freeze-dried. The procedure gives 0.205 g. of the captioned compound (43 %).

IR(KBr): 1771, 1667, 1605 cm$^{-1}$ UV$\lambda$max($\epsilon$ in water): 233 nm(10,800), 296 nm(17,600) NMR(d$_6$-DMSO)$\delta$: 2.83(m, morpholine $\beta$—CH$_2$), 2.98(m, —CH$_2$—morpholino), 3.4 – 4.0(m, 2—CH$_2$ and morpholine $\alpha$—CH$_2$ and —CH$_2$CO), 4.25(m, =NOCH$_2$—), 5.09(d, J=5Hz, 6—H), 5.64(q, J=5 and 8 Hz, 7—H), 6.91(thienyl 3— and 5—H), 7.30(thienyl 4—H), 8.30(s, —CH=N—), 9.13(d, J=8Hz, —CONH—)

Example 5

(1) 7$\beta$-amino-3-(2-morpholinoethoxy)iminomethyl-3-cephem-4-carboxylic acid

In a mixture of N, N-dimethylaniline (5.32 ml.) and dichloromethane (40 ml.) is suspended 7$\beta$-[D-5-(p-t-butylbenzoyl)amino-5-carboxyvaleramido]-3-(2-morpholinoethoxy) iminomethyl-3-cephem-4-carboxylic acid (4.62 g.). The suspension is chilled to −10° C and stirred. At a temperature not exceeding −10° C, phosphorus trichloride (1.575 ml.) is added dropwise and the mixture is stirred for 1 hour, whereupon a homogeneous solution is obtained. The solution is chilled to −20° C and phosphorus pentachloride (2.916 g.) is added. The mixture is stirred for 2 hours. Then, the reaction mixture is chilled to −50° C and cold methanol (26 ml.) is added dropwise, care being taken to keep the temperature below −35° C. The temperature is gradually increased to −5° C, at which temperature the mixture is stirred for 30 minutes. Following the addition of 20 ml. of water, the aqueous layer is adjusted to pH 3.5 with aqueous ammonia. After vigorous stirring, the aqueous layer is separated. The organic layer is further extracted with water (20 ml. × 3). The aqueous layers are pooled and concentrated under reduced pressure to 20 ml. This concentrate is run onto a chromatographic column of polystyrene resin (Amberlite XAD-2) and developed with water. The fractions containing the desired product are combined and freeze-dried. The procedure gives the above-indicated compound.

Yield 2.2 g. IR(KBr): 1788 cm$^{-1}$. NMR(D$_2$O)δ: 3.2 – 4.9(m, 14H), 5.20(d, J=5Hz), 6—H), 5.56(d, J=5Hz), 8.57(s, —CH=NO—).

(2) Sodium 7β-(D-α-sulfophenylacetamido)-3-(2-morpholinoethoxy)-iminomethyl-3-cephem-4-carboxylate In 15 ml. of water is dissolved 7β-amino-3-(2-morpholinoethoxy)iminomethyl-3-cephem-4-carboxylic acid (0.712 g.), and the solution is adjusted to pH 6 with 1N aqueous sodium hydroxide solution. To this solution is added a solution of D-(-)-α-sulfophenylacetylchloride (0.47 g.) in ethyl acetate (2 ml.) drop by drop while the reaction mixture is maintained at pH 6 to 7 by the addition of 1N aqueous sodium hydroxide solution. After the dropwise addition has been completed, the mixture is stirred for 30 minutes and, then, the ethyl acetate is distilled off under reduced pressure. The residue is chromatographed on a column of polystyrene resin (Amberlite XAD-2) and developed with water. The fractions containing the desired product are combined and freeze-dried. The procedure gives the above-indicated compound.

Yield 0.4 g. (35 %). IR(KBr): 1768, 1670, 1606 cm$^{-1}$. NMR(D$_2$O)δ: 3.35 – 4.20(12H, m), 4.52(m, —CH$_2$ON=), 5.15(s, C$_6$H$_5$-CH=), 5.24(d, J=5Hz, 6-H), 5.79(d, J=5Hz, 7—H), 7.3 – 7.8(m, phenyl), 8.25(s, —CH=NO—)

Example 6
7β-(D-mandelylamido)-3-(2-morpholinoethoxy)iminomethyl-3-cephem-4-carboxylic acid In dry dimethylformanide (10 ml.) is dissolved 7β-amino-3-(2-morpholinoethoxy)iminomethyl-3-cephem-4-carboxylic acid (0.712 g.) and, the, D-mandelic acid carboxy anhydride (0.356 g.). The mixture is stirred at room temperature, whereupon carbon dioxide gas is evolved to give a homogeneous reaction mixture. After 1 hour, cold water (10 ml.) is added to the reaction mixture. The mixture is then subjected to column chromotography on polystyrene resin (Amberlite XAD-2) and developed with water and, then, with 10 % aqueous ethanol. The fractions containing the desired product are combined and, after the ethanol is distilled off under reduced pressure, freeze-dried. The procedure gives the above-indicated compound.

Yield 0.259 g. (27 %). IR(KBr): 1780, 1675, 1605, 1510 cm$^{-1}$. UV λ max (ε in water): 296 nm(19,000).

NMR(d$_6$-DMSO): 2.6 – 3.15(m, morpholine β—CH$_2$ and —CH$_2$N=), 3.47 and 3.82(ABq, J=18Hz, 2-CH$_2$), 3.70(m, morpholine α—CH$_2$), 4.26(m, —CH$_2$ON=), 5.07(s, C$_6$H$_5$CH(OH)—). 5.08(d, J=5Hz, 6—H), 5.68(q, J=5 and 8Hz, 7—H), 7.15 – 7.55(m, C$_6$H$_5$—), 8.29(s, —CH=NO—), 8.66(d, J=8Hz, —NH—)

Elemental analysis: Calcd. for C$_{22}$H$_{26}$N$_4$O$_7$S.2H$_2$O. C, 50.18; H, 5.74; N, 10.64. Found: C, 50.69; H, 5.71; N, 10.64.

Example 7
(1) Sodium 7β-(D-mandelylamido)-3-hydroxymethyl-3-cephem-4-carboxylate To 7β-(D-mandelylamido)-3-acetoxymethyl-3-acetoxymethyl-3-cephem-4-carboxylic acid (4.06 g.) are added water (20 ml.) and sodium bicarbonate (0.84 g.), whereby the acid is converted to a salt. To this aqueous solution is added phosphate buffer (pH 7.2, 100 ml.) and, then, lipase "Saiken 100" (manufactured by Osaka Saikin Kenkyusho) (4.77 g.), and the system is stirred at a constant temperature of 30° C and at pH about 7.2 for 16 hours. The reaction mixture is filtered under suction (with Hyflo-Supercel as filter aid) and the filtrate is concentrated under reduced pressure. The concentrate is placed onto a column of Amberlite XAD-2 and developed with water. The fractions containing the desired product are collected and concentrated under reduced pressure. The concentrate is freeze-dried, whereupon the desired product is obtained.

(2) 7β-(D-mandelylamido-9-oxo-11-hydroxy-11H-furano-(4,3-c)-3-cephem

In acetone (100 ml.) is suspended sodium 7β-(D-mandelylamido)-3-hydroxymethyl-3-cephem-4-carboxylate (1.93 g.) and under stirring and cooling at −3° C, the reagent mentioned below (see Note) (1.25 ml.) is added over a period of 5 minutes. The mixture is further stirred at 0° C for 1 hour, after which time the acetone is distilled off under reduced pressure. The residue is diluted with water (100 ml.) and extracted three times with ethyl acetate (150 ml.). The extract is washed twice with a saturated aqueous solution (300 ml.) of sodium chloride, dried over anhydrous sodium sulfate, and concentrated to dryness. The procedure gives the above-indicated compound.

Yield 1.41 g. (78 %) IR(KBr): 1787, 1673 cm$^{-1}$ $^{NMR(D}$-DMSO + D$_2$0)δ: 3.4 – 3.8(m, 2—CH$_2$), 5.09(s, C$_6$H$_5$— CH(OH)—), 5.10(d, J=5Hz), 5.80(d, J=5Hz, 7-H), 6.21

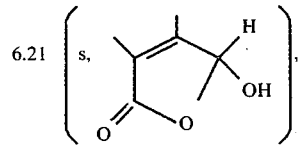

6.21 ⎧ s, ⎫
7.2 – 7.5(m, C$_6$H$_5$—)

(Note) reagent: A mixture of 2.67 g. chromic anhydride and 2.26 ml. concentrated sulfuric acid is diluted with water to make 10 ml.

(3) 7β-(D-mandelylamido)-3-(2-morpholinoethoxy)iminomethyl-3-cephem-4-carboxylic acid In dry dimethylsulfoxide (3 ml.) is dissolved 7β-(D-mandelylamido)-9-oxo-11-hydroxy-11H-furano(4,3-c)-3-cephem(0.08 g.), followed by the addition of 0-(2-morpholinoethyl)hydroxylamine dihydrochloride (0.06 g.). The mixture is stirred at room temperature for 30 minutes and anhydrous sodium acetate (0.022 g.) is added. The mixture is further stirred at room temperature for 30 minutes. To the reaction mixture is added cold water (5 ml.) and the mixture is run onto a column of polystyrene resin (Amberlite XAD-2) which is eluted with water and, then, with 10 % aqueous ethanol. The fractions containing the desired product are pooled and the ethanol is distilled off under reduced pressure. Finally the residue is freeze-dried to obtain the above indicated compound.

Yield 0.077 g. (71 %)

In IR, NMR and TLC, this product is in good agreement with the product obtainable according to Example 6.

EXAMPLE 8

7β-(cyanoacetamido)-3-(2-morpholinoethoxy)iminomethyl-3-cephem-4-carboxylic acid.

In dry dimethylsulfoxide (3 ml.) is dissolved 7β-(cyanoacetamido)-9-oxo-11-hydroxy-11H-furano-(4,3-c)-3-cephem (0.08 g.), followed by the addition of 0-(2-morpholinoethyl)hydroxylamine dihydrochloride (0.06 g.). The mixture is stirred at room temperature for 30 minutes, after which time anhydrous sodium acetate (0.022 g.) is added over a lperiod of about 1 hour. The mixture is further stirred for 30 minutes. Following the addition of cold water (5 ml.), the mixture is subjected to column chromatography on polystyrene resin (Amberlite XAD-2).

The chromatogram is developed with water and, then, with 5% aqueous ethanol. The fractions containing the desired product are pooled and the ethanol is distilled off under reduced pressure. Finally the residue is freeze-dried to obtain the above-indicated compound.

Yield 0.077 g. (67%). IR(KBr): 2250(CN), 1778, 1688, 1607, 1570 cm$^{-1}$. UVλmax (ε in water): 296 nm(19,900). NMR(D$_2$O)δ: 1 – 4.3(14H, m), 3.92(s, NC—C$\underline{H}_2$—CO), 5.33(d, J=5Hz, 6—H), 5.81(d, J=5Hz, 7—H), 8.32(s, —CH=NO—)

EXAMPLE 9

7β-(D-mandelylamido)-3-(2-morpholino-1-methylethoxy) iminomethyl-3-cephem-4-carboxylic acid In dry dimethylsulfoxide (8 ml.) is dissolved 7β-(D-mandelylamido)-9-oxo-11-hydroxy-11H-furano-(4,3-c)-3-cephem(0.362 g.), followed by the addition, in a single dose, of 0-(2-morpholino-1-methylethyl)hydroxylamine dihydrochloride (0.233 g.). The mixture is stirred at room temperature for 30 minutes, after which time anahydrous sodium acetate (0.082 g.) is added over a period of 40 minutes. Then, the mixture is further stirred at room temperature for 1.5 hours. Under cooling with ice, a solution of 0.164 g. sodium acetate in 8 ml. water is added to the above mixture. The mixture is then chromatographed on a column of polystyrene resin (Amberlite XAD-2) and developed with water, 10 % aqueous ethanol and 15 % aqueous ethanol in the order mentioned. The fractions containing the desired product are pooled and the ethanol is distilled off under reduced pressure. Finally the residue is freeze-dried to obtain the above-indicated compound.

Yield 0.221 g. (44 %). IR(KBr): 1777, 1670, 1607 cm$^{-1}$. UVλmax (ε in water): 295 nm(18,900) NMR(D$_6$—DMSO + D$_2$O)ε: 1.24 and 1.26(each d, J=6Hz, O—CH(C$\underline{H}_3$)—), 3.10(m, morpholine β—CH$_2$ and —CH$_2$-N=), 3.47 and 3.78 (ABq, J=18Hz, 2—CH$_2$), 3.84(m, morpholine α—CH$_2$),
4.25(m, NO—C$\underline{H}$(CH$_3$)—), 5.06(d, J=5Hz, 6—H), 5.09(s, C$_6$H$_5$—C$\underline{H}$(OH)-), 5.63(d, J=5Hz, 7—H, 7.2 – 7.5(m, C$_6$$\underline{H}_5$—), 8.30 and 8.33(each s, —C$\underline{H}$=NO)

Elemental analysis: Calcd. for C$_{23}$H$_{28}$N$_4$O$_7$S.2.5H$_2$O: C, 50.26; H, 6.05; N, 10.19; Found: C, 50.58; H, 6.00; N. 9.99

EXAMPLE 10

7β-(D-mandelylamido)-3-morpholinopropoxy) iminomethyl-3-cephem-4-carboxylic acid In dry dimethylsulfoxide (8 ml.) is dissolved 7β-(D-mandelylamido)-9-oxo-11-hydroxy-11H-furano-(4,3-c)-3-cephem (0.362 g.) and, then, O-(3-morpholinopropyl)hydroxylamine dihydrochloride (0.233 g.) is added in a single dose. The mixture is stirred at room temperature for 30 minutes, after which time anhydrous sodium acetate (0.082 g.) is added over a period of 1.5 hours. The mixture is further stirred at room temperature for 30 minutes. Under cooling with ice, a solution of 0.164 g. sodium acetate in 8 ml. water is added to the above reaction mixture. The mixture is then chromatographed on a column of polystyrene resin (Amberlite XAD-2) and developed with water and, then, with 12.5 % aqueous ethanol. The fractions containing the desired product are pooled and the ethanol is distilled off under reduced pressure.

Finally the residue is freeze-dried to obtain the above-indicated compound.

Yield 0.21 g. (42 %) IR(KBr): 1778, 1674, 1607 cm$^{-1}$.

UVλmax (ε in water): 296 nm(15,700).

NMR(d$_6$—DMSO + D$_2$O): 2.05(m, CH$_2$C$\underline{H}_2$CH$_2$N), 3.17(m, morpholine β—CH$_2$ and —CH$_2$n=), 3.3 – 3.9(m, morpholine α—CH$_2$ $_{and}$ 2-CH$_2$), 4.0 – 4.4(m, NOC$\underline{H}_2$—), 4.99(d, J=5Hz, 6—H),
5.07(s, C$_6$H$_5$-C$\underline{H}$(OH)—), 5.59(d, J=5Hz, 7—H), 7.2– 7.5(m, C$_6$$\underline{H}_5$—), 8.26(s, —C$\underline{H}$=N—)

analysis: Calcd. for C$_{23}$H$_{28}$—4O$_7$s.2.5H$_2$O; C, 50.26; H, 6.05; N, 10.19; Found: C, 50.46; H, 5.70; N, 9.92

EXAMPLE 11

7β-(D-mandelylamido)-3-[2-morpholino-(1-methoxymethyl)ethoxy]iminomethyl-3-cephem-4-carboxylic acid In dry dimethylsulfoxide (6 ml.) is dissolved 7β-(D-mandelylamido)-9-oxo-11-hydroxy-11H-furano-(4,3-c)-3-cephem(0.362 g.) and, then, 0-(2-morpholino-1-methoxymethylethyl)hydroxylamine dihydrochloride (0.263 g.) is added in a single dose. The mixture is stirred at room temperature for 30 minutes, after which time anhydrous sodium acetate (0.082 g.) is added over a period of 1 hour. The mixture is further stirred at room temperature for 30 minutes, after which a solution of sodium acetate (0.164 g.) in water (6 ml.) is added. The mixture is chromatographed on a column of polystyrene resin (Amberlite XAD-2) and developed with water, 12.5% aqueous ethanol and 15 % aqueous ethanol in the order mentioned. The fractions containing the desired product are pooled and the ethanol is distilled off under reduced pressure. Finally the residue is freeze-dried to obtain the above-indicated compound.

Yield 0.228 g. (43 %) IR(KBr): 1779, 1676; 1608 cm$^{-1}$. NMR(d6—DMSO)δ: 2.70(m, morpholino β—CH$_2$), 2,98(m, —CH$_2$N=), 3.21(s, CH$_3$O), 3.3 – 3.9(m, 2-CH$_2$, morpholino α-CH$_2$ and —CH$_2$O—), 4.17(m, =C$\underline{H}$—CH$_2$N), 5.10(s, C$_6$H$_5$— C$\underline{H}$(OH)—), 5.12(d, J=5Hz, 6—H), 5.71(q, J=5 and 8Hz, 7—H), 7.1 – 7.5(m, C₆H₅—), 8.28(s, —C<u>H</u>=N—), 8.71(d, J=8Hz, —COHN—).

What is claimed is:

1. A compound of the formula:

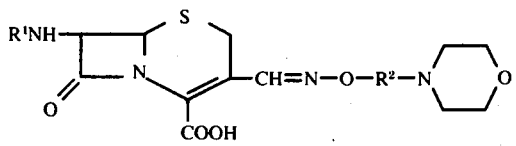

wherein R¹ is formyl, benzoyl or a group having the formula:

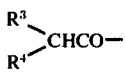

wherein R³ is hydrogen, phenyl, phenoxy, thienyl, tetrazolyl, furyl, pyrazolyl, pyridyloxy, cyclohexenyl, acetyl, cyano, 3-amino-3-carboxypropyl or 3-amino-3-carboxypropyl in which the 3-amino group is protected with isobornyloxycarbonyl, β-methylsulfonylethoxycarbonyl, benzoyl, phathalyl, p-t-butylbenzoyl, phenylacetyl, phenylthiocarbonyl, benzyloxycarbonyl, p-toluenesulfonyl, or p-t-butylbenzenesulfonyl, and R⁴ is hydrogen, hydroxyl, sulfo, carboxyl or C₁₋₂ alkyl, and R² is unsubstituted C₁₋₄ alkylene or substituted C₁₋₄ alkylene substituted with methoxy or ethoxy, or a pharmaceutically acceptable salt thereof.

2. A compound according to claim 1, wherein R⁴ is hydrogen and wherein R³ is phenyl, phenoxy, thienyl, tetrazolyl, furyl, pyrazolyl, pyridyloxy, cyclohexenyl, acetyl or cyano.

3. A compound according to claim 2, wherein R³ is phenyl, thienyl or cyano group.

4. A compound according to claim 1, wherein R³ is phenyl, phenoxy, thienyl, tetrazolyl, furyl, pyrazolyl, pyridyloxy, cyclohexenyl or acetyl, and R⁴ is hydroxyl, sulfo, carboxyl or alkyl.

5. A compound according to claim 1, wherein the acyl group is 5-protected or unprotected amino-5-carboxyvaleryl group.

6. A compound according to claim 1, wherein R³ is phenyl, phenoxy, pyridyloxy, thienyl, tetrazolyl, furyl, pyrazolyl or cyclohexenyl.

7. A compound according to claim 6, wherein R³ is phenyl, phenoxy or pyridyloxy.

8. A compound according to claim 1, wherein said unsubstituted C₁₋₄ alkylene group is selected from the group consisting of methylene ethylene, trimethylene, tetramethylene, 1-methylethylene, 2-methylethylene, 1-methylpropylene, 2-methylpropylene, 3-methylpropylene and 1,1-dimethylethylene.

9. A compound according to claim 6, wherein said unsubstituted C₁₋₄ alkylene group is selected from the group consisting of methylene, ethylene, trimethylene, tetramethylene, 1-methylene, 2-methylethylene, -methylethylene -methylpropylene, 2-methylpropylene, 3-methylpropylene and 1,1-dimethylethylene.

10. A compound according to claim 1, wherein said compound is an acid.

11. A compound according to claim 1, wherein said compound is a pharmaceutically acceptable salt.

12. A compound according to claim 1 wherein R⁴ is hydrogen, hydroxyl, sulfo or carboxyl.

13. A compound of the formula:

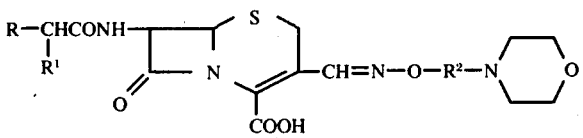

wherein R is 3-(p-t-butylbenzoyl)amino-3-carboxypropyl, 3-(p-t-butylbenzenesulfonyl)amino-3-carboxypropyl, phenyl, thienyl or cyano, R¹ is hydrogen, hydroxyl or sulfo and R₂ is unsubstituted C₂₋₃ alkylene or substituted C₁₋₄ alkylene substituted with methoxy, or a pharmaceutically acceptable salt thereof.

14. A compound claimed in claim 1, which is 7β-[D-5-(p-t-butylbenzoyl)amino-5-carboxyvalerylamido]-3-(2-morpholinoethoxy)iminomethyl-3-cephem-4-carboxylic acid.

15. A compound claimed in claim 1, which is 7β-[D-5-(p-t-butylbenzenesulfonyl)amino-5-carboxyvalerylamido]-3-(2-morpholinoethoxy)iminomethyl-3-cephem-4-carboxylic acid.

16. A compound claimed in claim 1, which is 7β-(phenylacetamido)-3-(2-morpholinoethoxy)iminomethyl-3-cephem-4-carboxylic acid.

17. A compound claimed in claim 1, which is 7β-(2-thienylacetamido)-3-(2-morpholinoethoxy)iminomethyl-3-cephem-4-carboxylic acid.

18. A compound claimed in claim 1, which is 7β-(D-α-sulfophenylacetamido)-3-(2-morpholinoethoxy)iminomethyl-3-cephem-4-carboxylic acid.

19. A compound claimed in claim 1, which is 7β-(D-mandelylamido)-3-(2-morpholinoethoxy)iminomethyl-3-cephem-4-carboxylic acid.

20. A compound claimed in claim 1, which is 7β-cyanoacetamido-3-(2-morpholinoethoxy)iminomethyl-3-cephem-4-carboxylic acid.

21. A compound claimed in claim 1, which is 7β-(D-mandelylamido)-3-(2-morpholino-1-methylethoxy)iminomethyl-3-cephem-4-carboxylic acid.

22. A compound claimed in claim 1, which is 7β-(D-mandelylamido)-3-(3-morpholinopropoxy)iminomethyl-3-cephem-4-carboxylic acid.

23. A compound claimed in claim 1, which is 7β-(D-mandelylamido)-3-[2-morpholino-(1-methoxymethyl)ethoxy]-iminomethyl-cephem-4-carboxylic acid.

* * * * *